United States Patent [19]

Suami et al.

[11] Patent Number: 4,744,975
[45] Date of Patent: May 17, 1988

[54] 6-IODOETHYLATED STARCH AND PROCESS FOR PREPARING THE SAME

[75] Inventors: Tetsuo Suami, Musashino; Masao Sako, Kobe, both of Japan

[73] Assignee: Nippon Universal Pharmaceutical Co., Ltd., Tokyo, Japan

[21] Appl. No.: 865,347

[22] Filed: May 20, 1986

[30] Foreign Application Priority Data

May 28, 1985 [JP] Japan ................................. 60-113300

[51] Int. Cl.⁴ ............................................. A61K 49/04
[52] U.S. Cl. ........................................ 424/5; 524/47; 536/102; 536/103; 536/14; 536/105; 536/106; 536/107; 536/108; 536/109; 536/110; 536/111
[58] Field of Search ............... 536/102, 103, 104, 105, 536/106, 107, 108, 109, 110, 111; 524/47; 424/5

[56] References Cited

U.S. PATENT DOCUMENTS 4,119,487 10/1978 Tessler ................................. 536/108
4,167,621 9/1979 Tessler ................................. 536/108

Primary Examiner—C. Warren Ivy
Assistant Examiner—Alex H. Walker
Attorney, Agent, or Firm—Frishauf, Holtz, Goodman & Woodward

[57] ABSTRACT

6-Iodoethylated starch and process for preparing the same are disclosed. The 6-idodethylated starch contains one iodine attached per 5 glucose units. Said compound is useful as a contrast agent for X-ray examination, especially for opacifying the vascular os lymphatic vessel. Said compound is produced by reacting 6-hydroxyethylated starch with N-iodosuccinimide in the presence of triphenylphosphine.

8 Claims, No Drawings

6-IODOETHYLATED STARCH AND PROCESS FOR PREPARING THE SAME

BACKGROUND OF THE INVENTION

1. Field of the Invention

This invention relates to 6-iodoethylated starch and a process for preparing the same. More particularly, it is concerned with 6-iodoethylated starch in which one iodine is attached per 5 glucose units and a process for preparing the same.

The 6-iodoethylated starch in the present invention is a novel compound which has not been disclosed in any literature. It is useful as a contrast agent for X-ray examination, especially for opacifying the vascular and lymphatic vessels.

2. Description of Prior Arts

As instruments for the radiographic diagnosis were diffused and diagnostic methods including computer tomography (CT) were developed in recent years, use of contrast agents for diagnosis has been much increased in therapeutic practice.

Contrast agents for the vascular vessels currently widely used are those which comprise an iodine compound of benzoic acid as the opacifying component. Whereas these contrast agents are highly capable of opacifying the vessels under X-ray examination, they cause pain or feeling of heat in patients on introduction into the blood vessel. In addition, they are apt to cause allergic reactions of various degrees, and occasionally death due to severe anaphylactic reactions are reported.

On the other hand, the lymphatic vessel-contrast agent primarily used is the ethyl ester of poppy oil-fatty acids. The contrast agent, which comprises oily iodine compounds, is not leaked through the wall of the lymphatic vessels to reach the desired site and causes the vessels to cast distinct densities. However, since composition of the agent is oily, it may cause embolization of the peripheral blood vessels when passed from the lymphatic system to the vascular system. It is known that there are caused pulmonary embolisms frequently as well as severe adverse reactions such as cerebral infarction.

In view of the difficulties discussed above, development of safer and superior contrast agents has been desired.

SUMMARY OF THE INVENTION

As a result of extensive studies to provide safer and superior contrast agents free from the above-mentioned problems, we have completed the present invention.

According to the invention, there is provided 6-iodoethylated starch in which one iodine is attached per 5 glucose units.

Further according to the invention, a process for preparing the above-mentioned 6-iodoethylated starch which comprises reacting 6-hydroxyethylated starch with N-iodosuccinimide in the presence of triphenylphosphine is provided. The 6-iodoethylated starch of the invention has the following physicaochemical properties:

Melting point: 165° C. (decomposed);

Specific optical rotation: $[\alpha]_D^{22} +136°$ (C=1.45, $H_2O$);

IR: $\gamma_{max}^{KBr}$ cm$^{-1}$:3400, 2920, 1655, 1360, 1210, 1150, 1020, 685;

Solubility in water: 0.5 g/ml;

Elementary analysis: Calc'd. % (for one iodine attached per 5 glucose units): C 41.07; H 5.50; I 12.05, Found %: C 37.31; H 5.42; I 12.47.

DETAILED DESCRIPTION OF THE INVENTION

In the compound of the invention, iodine is believed to be substituted for the primary hydroxyl group of 6-hydroxyethylated starch and is attached in a proportion of one per 5 glucose units. Iodine content is approximately 12%. If the iodine content is lower than 12%, the contrast capacity will not be sufficient. On the other hand, if it exceeds 12%, the solubility in water will be reduced, and if it is over 15%, the compound will be insoluble.

The 6-iodoethylated starch of the invention is prepared by reacting 6-hydroxyethylated starch with N-iodosuccinimide in the presence of triphenylphosphine.

The starting 6-hydroxyethylated starch used in the above preparative process is a compound known as a plasma expander. It is produced by converting waxy starch primarily composed of amylopectin to an ether with ethylene oxide, followed by acid hydrolysis (U.S. Pat. No. 3,523,938). The reaction according to the invention is carried out desirably using an appropriate organic solvent such as dimethylformamide or methylcellosolve. The reaction temperature and time are 40°–150° C. and 5–50 hours, respectively. The amount of N-iodosuccinimide used is suitably 0.45 g per gram of the starting 6-hydroxyethylated starch. The amount of triphenylphosphine used is about 0.52 g/g. After completion of the reaction, the desired product is isolated from the reaction product in a conventional fashion. For example, to the reaction mixture is added an alcohol such as methanol to decompose an excess of the reagents, followed by addition of an appropriate organic solvent such as chloroform and then extraction with water. The extract, after deionized with an ion exchange resin if needed, is concentrated under reduced pressure. To the concentrate is added an alcohol such as ethanol. Precipitates thus formed are collected to obtain the desired 6-iodoethylated starch.

The compound of the invention thus obtained exerts the physicochemical properties as listed above. It is also of superior properties as a contrast agent as described below.

In 2 ml of physiological saline solution (50% w/v) was dissolved 1 g of the compound of the invention. As control was employed a commercially available contrast agent, Natrium Meglumine Diatrizoate (urografin 76%), which was 1:2 diluted with physiological saline solution. The two test solutions in the same amount were encapsulated respectively in a polyethylene tube with the same inner diameter and subjected to X-ray photographing under the same conditions. Comparison was made of the intensity of the density on the film between the two. The intensity was measured by a densitometer. The result indicated that the control contrast agent exhibited a contrast capacity 2.6 times higher in terms of the intensity. This is because iodine content is 30% with the control compound and approximately 12% with the compound of the invention, the contrast capacity being dependent upon the iodine content of the whole molecule.

In anyway, as there is a tendency for the contrast agent to be used in approximately 1:2 dilution in recently employed processes such as CT and digital substraction angiography (DSA), contrast capacity of the compound of the invention is sufficiently high.

The compound of the invention is used in the same way as with prior-art X-ray contrast agents. For example, X-ray picture is taken while introducing the compound of the invention dissolved in distilled water or physiological saline solution (50% w/v) into the vascular or lymphatic vessel.

As the compound of the invention is rapidly decomposed in about 20 minutes after introduced into the vascular or lymphatic vessel, there is no problem of residual toxicity. Since the above-mentioned duration is sufficiently long to take X-ray picture, the above-mentioned feature of the compound of the invention is very favorable as the contrast agent.

One gram of the compound of the invention is dissolved in 2 ml of physiological saline solution, and the whole solution is intramuscularly injected in a rabbit weighing 3 kg, at the forelimb. When the rabbit was sacrificed and examined after a week, no particular gross abnormalities were observed.

Aslo, a 40% w/v distilled water solution of the compound of the invention was introduced into a rabbit at a dose of 3 ml per kg bodyweight at a rate of 1 ml/minute. There was observed no death during 14 days of observation.

The invention will be described in more details below by means of examples.

EXAMPLE 1

To a stirred suspension of 6-hydroxyethylated starch (6 HES, 10.0 g) in anhydrous dimethylformamide (DMF, 80 ml), was added triphenylphosphine (5.2 g). After stirring at room temperature for 40 mins., a solution of N-iodosuccinimide (4.5 g) in anhydrous DMF (20 ml) was slowly added to the suspension over 30 mins. under ice cooling. The reaction mixture was agitated for 19 hrs. at 70° C. followed by addition of methanol (20 ml). After stirring at room temperature for 2 hrs., the reaction mixture was concentrated under reduced pressure to a volume of 80 ml. Chloroform (100 ml) was added to the residue and the resulting solution was extracted with water (100 ml). The aqueous layer was washed twice with chloroform (2×100 ml) and deionized with ion-exchange resins Amberlite IR 120 (H+ type, 25 ml) and Amberlite IRA 400 (OH− type, 25 ml), successively. The deionized solution was concentrated under reduced pressure to a volume of 20 ml. Absolute ethanol (100 ml) was added to the residual solution, and precipitates were collected by filtration to give 8.2 g of a crude product. The product was dissolved in water, and the aqueous solution was deionized again with the above-mentioned ion-exchange resins. The solution was concentrated under reduced pressure, and to the residual solution (20 ml) was added absolute ethanol (100 ml) to give the desired product 6-iodoethylated starch (4.4 g). The product has the following physicochemical properties:

Melting point: 165° C. (decomposed);

Specific optical rotation: $[\alpha]_D^{22} + 136°$ (C=1.45, H$_2$O);

IR: $\gamma_{max}^{KBr}$ cm$^{-1}$:3400, 2920, 1655, 1360, 1210, 1150, 1020, 685;

Elementary analysis: Calc'd. % (for one iodine attached per 5 glucose units): C 41.07; H 5.50; I 12.05. Found %: C 37.31; H 5.42; I 12.47.

The 6-iodoethylated starch of the invention has excellent properties as a contrast agent for X-ray examination, especially for opacifying the vascular or lymphatic vessels.

As a matter of fact, the compound of the invention which is a macromolecular compound will not be leaked from the wall of the lymphatic vessel; and the compound which is soluble in water will not be encountered with the problem of embolization in the peripheral blood vessel when passed to the vascular vessel. Moreover, the compound of the invention will not cause pain or feeling of heat when introduction into the vascular vessel. There will be caused no allergic reactions. Therefore, the compound can be employed as a safe contrast agent.

What is claimed is:

1. A 6-iodoethylated starch containing one iodine attached per 5 glucose units characterized by the following physicochemical properties:

Melting point: 165° C. (decomposed);
Specific optic rotation: $[\alpha]_D^{22} + 136°$ (C=1.45, H$_2$O);
IR: $\gamma_{max}^{KBr}$ cm$^{-1}$:3400, 2920, 1655, 1360, 1210, 1150, 1020, 685;
Solubility in water: 0.5 g/ml;
Elementary analysis: Calc'd % (for one iodine attached per 5 glucose units): C 41.07; H 5.50; I 12.05: Found %: C 37.31; H 5.42; I 12.47.

2. A process for preparing 6-iodoethylated starch according to claim 1 which comprises reacting 6-hydroxyethylated starch with N-iodosuccinimide in the presence of triphenylphosphine.

3. A method for opacifying a portion of a patient for x-ray examination comprising introducing into said portion an opacifying effective amount of the 6-iodoethylated starch of claim 4. The method of claim 3 wherein a vascular or a lymphatic vessel is to be opacified and the 6-iodoethylated starch is introduced by injection into said vessel.

5. The method of claim 3 wherein the x-ray examination is computer tomography or digital subtraction angiography.

6. A 6-iodoethylated starch containing approximately one iodine per 5 glucose units and having between about 12% up to 15% iodine by weight.

7. The 6-iodoethylated starch of claim 6 containing about 12% iodine.

8. A process for preparing the 6-iodoethylated starch of claim 6 which comprises reacting 6-hydroxyethylated starch with N-iodosuccinimide in the presence of triphenylphosphine.

* * * * *